(12) United States Patent
Stanton, Jr. et al.

(10) Patent No.: US 6,777,188 B2
(45) Date of Patent: Aug. 17, 2004

(54) GENOTYPING BY MASS SPECTROMETRIC ANALYSIS OF ALLELIC FRAGMENTS

(75) Inventors: Vincent P. Stanton, Jr., Belmont, MA (US); Jeffrey Olson, Chelmsford, MA (US); Jia Liu Wolfe, Winchester, MA (US); Martin Zillmann, Shrewsbury, MA (US)

(73) Assignee: Variagenics, Inc., Cambridge, MA (US)

( * ) Notice: Subject to any disclaimer, the term of this patent is extended or adjusted under 35 U.S.C. 154(b) by 0 days.

(21) Appl. No.: 10/107,751

(22) Filed: Mar. 26, 2002

(65) Prior Publication Data

US 2002/0150943 A1 Oct. 17, 2002

Related U.S. Application Data

(63) Continuation-in-part of application No. 09/394,467, filed on Sep. 10, 1999, now Pat. No. 6,566,059.
(60) Provisional application No. 60/149,533, filed on Aug. 17, 1999, and provisional application No. 60/102,724, filed on Oct. 1, 1998.

(51) Int. Cl.[7] ........................... C12Q 1/68; C12P 19/34; C07H 21/00
(52) U.S. Cl. ................... 435/6; 435/91.1; 435/91.2; 536/23.1
(58) Field of Search .................. 435/6, 91.1, 91.2; 536/23.1

(56) References Cited

U.S. PATENT DOCUMENTS

| | | | |
|---|---|---|---|
| 4,701,419 A | 10/1987 | Morris | 436/89 |
| 4,879,214 A | 11/1989 | Kornher et al. | 435/91 |
| 5,003,059 A | 3/1991 | Brennan | 536/27 |
| 5,064,754 A | 11/1991 | Mills | 435/6 |
| 5,174,962 A | 12/1992 | Brennan | 422/78 |
| 5,187,085 A | 2/1993 | Lee | 435/91 |
| 5,221,518 A | 6/1993 | Mills | 422/62 |
| 5,332,666 A | 7/1994 | Prober et al. | 435/91.5 |
| 5,424,184 A | 6/1995 | Santamaria et al. | 435/6 |
| 5,547,835 A | 8/1996 | Köster | 435/6 |
| 5,552,278 A | 9/1996 | Brenner | 435/6 |
| 5,580,733 A | 12/1996 | Levis et al. | 435/6 |
| 5,605,798 A | 2/1997 | Köster | 435/6 |
| 5,622,824 A | 4/1997 | Köster | 435/6 |
| 5,691,141 A | 11/1997 | Köster | 435/6 |
| 5,700,642 A | 12/1997 | Monforte et al. | 435/6 |
| 5,830,655 A | 11/1998 | Monforte et al. | 435/6 |
| 5,869,242 A | 2/1999 | Kamb | 435/6 |
| 5,939,292 A | 8/1999 | Gelfand et al. | 435/91.2 |

FOREIGN PATENT DOCUMENTS

WO  WO98/00433  1/1998

OTHER PUBLICATIONS

Andersson, B. et al., "Simultaneous Shotgun Sequencing of Multiple cDNA Clones," *DNA Sequence*, 1997, 7:63–70.

Astatke, M., et al., "Deoxynucleoside Triphosphate and Pyrophosphate Binding Sites in the Catalytically Competent Ternary Complex for the Polymerase Reaction Catalyzed by DNA Polymerase I (Klenow Fragment)," *J. Biol. Chem.*, 1995, 270: 1945–54.

Astatke, M., et al., "How *E. coli* DNA polymerase I (Klenow Fragment) Distinguishes Between Deoxy–and Dideoxy–nucleotides," *J. Mol. Biol.*, 1998, 278:147–165.

Astatke, M., et al., "A Single Side Chain Prevents *Escherichia coli* DNA Polymerase I (Klenow Fragment) from Incorporating Ribonucleotides," *Proc. Nat. Acad. Sci. USA*, 1998, 95:3402–3407.

(List continued on next page.)

*Primary Examiner*—Jezia Riley
(74) *Attorney, Agent, or Firm*—Bernard F. Rose; Bingham McCutchen LLP (57) ABSTRACT

The present invention relates to a method for genotyping a diploid organism by cleaving segments of two alleles such that 7–20 nucleotide fragments that contain a suspected polymorphic locus are produced and comparing the masses of those fragments.

21 Claims, 4 Drawing Sheets

OTHER PUBLICATIONS

Barnes, W.M., "DNA Sequencing by Partial Ribosubstitution," *J. Mol. Bio.*, 1978, 119:83–99.

Barnes, W.M., "PCR Amplication of Up to 35–kb DNA with High Fidelity and High Yield from λ Bacteriophage Templates," *Proc. Natl. Acad. Sci.* USA, 1994, 91:2216–2220.

Beavis, R., et al "Matrix–Assisted Laser Desorption/Ionization Mass Spectrometry of Biopolymers," *Anal. Biochem.*, 1991, 63: 1193–1203.

Chen, C. N., et al, "Ordered Shotgun Sequencing of a 135 kb Xq25 YAC Containing ANT2 and Four Possible Genes, including Three Confirmed by EST Matches," *Nucleic Acids Research*, 1996, 24:4034–4041.

Daugherty P.S., et al., "Antibody Affinity Maturation Using Bacterial Surface Display," *Protein Eng* 1998, 11:825–32.

Delarue, M., et al., "An Attempt to Unify the Structure of Polymerases," *Protein Eng*, 1990, 3:461–467.

Fichant, G. A. and Quentin, Y., "A Frameshift Error Detection Algorithm for DNA Sequencing Projects," *Nucleic Acid Research*, 23:2900–2908, 1995.

Fu, D. J., et al., "Sequencing Exons 5 to 8 of the p53 Gene by MALDI–TOF Mass Spectrometry," *Nature Biotechnology*, 1998, 16:381–384.

Giese, B., et al, "The Chemistry of Single–Stranded 4'–DNA Radicals: Influence of the Radical Precursor o Anaerobic and Aerobic Strand Cleavage," *Chemistry & Biology*, 1995, 2 No. 6, 367–375.

Giese, B., et al, "The Mechanism of Anaerobic, Radical–Induced DNA Strand Scission," Agnew. *Chem. Int. Ed. Engl.* 1993, 32:1742–43.

Gish, G., et al "DNA and RNA Sequence Determination Based on Phosphorothioate Chemistry," *Reports*, 1988 1520–1522.

Gupta and Kool, "A Self–Cleaving DNA Nucleoside," *Chem. Commun.* 1997, pp 1425–26.

Harayama, S., "Artificial evolution by DNA shuffling," *Trends Biotechnol.*, 1998, 16:76–82.

Hentosh, P. et al, "Ploymerase Chain Reaction Amplification of Single–Stranded DNA Containing a Base analog, 2–Chloroadenine," *Anal. Biochem.*, 1992, 201:277–281.

Huang, Y., "Determinants of Ribose Specificity in RNA Polymerization: Effects of $Mn^{2+}$ and Deoxynucleoide Monophosphate Incorporation into Transcripts," *Biochemistry*, 1997, 36:13718–13728.

Joyce, C. M., "Choosing the Right Sugar: How Polymerases Select a Nucleotide Substrate," *Proc. Natl. Acad. Sci.* USA 1997, 94:1619–1622.

Kaczorowski, T., et al., "Assembly of 18–Nucleotide Primers by Ligation of Three Hexamers: Secuqncing of Large Genomes by Primer Walking," *Anal. Biochem.*, 1994, 221:127–135.

Khurshid, F., et al, "Error Analysis in Manual and Automated DNA Sequencing," *Analytical Biochemistry*, 208:138–143, 1993.

Kirpekar, F., et al, "Matrix–Assisted Laser Desorption–Ionization Mass Spectrometry of Enzymatically Synthesized RNA up to 150 kDa," *Nucleic Acids Research*, 1994, 22: No. 19 3866–3870.

Kristensen, T., et al, "An Estimate of the Sequencing Error Frequency in the DNA Sequence Databases," *DNA Sequencing*, 2:343–346, 1992.

Landegren, U. et al., Reading Bits of Genetic Information: Methods for Single–nucleotide Polymorphism Analysis, *Genome Research* 1998, 88:769–76.

Liu, D., et al., "Bi–stranded, Multisite Replication of a Base Pair Between Difluorotoluene and Adenine: Confirmation by 'Inverse' Sequencing," *Chem. Biol.*, 4:919–929, 1997.

Lodhi, M. A., et al., "High–Quality Automated DNA Sequencing Primed with Hexamer Strings," *Genome Research*, 1996, 6:10–18.

Martin–Gallardo, et al., "Automated DNA Sequencing and Analysis of 106 Kilobases from Human Chromosome 19q13.3," *Nature Genetics*, 1992 1:34–39.

Marx, A., et al, "Synthesis of 4'–C–Acylated Thymidines," *Helv. Chim. Acta*, 1996, 79:1980–94.

Maxam and Gilbert, "A New Method for Sequencing DNA" *Proc. Nat. Acad. Sci.* USA, 74, 560–564 1977.

Moran, S., et al., "A Thymidine Triphosphate Shape Analog Lacking Watson–Crick Pairing ability is Replicated with High Sequence Selectivity," *Proc. Natl. Acad. Sci.* USA, 94:10506–10511, 1997.

Nakamaye, K. et al, "Direct Sequencing of Polymerase Chain Reaction Amplified DNA Fragments Through the Incorporation of Deoxynucleoside α–thiotriphosphates," *Nucleic Acid Research*, 1988, 16:9947–9959.

Nelson, R.W., et al, "Volatilization of High Molecular Weight DNA by Pulsed Laser Ablation of Frozen Aqueous Solutions," *Science* 1989, vol. 246, 1585–1587.

Nickerson, D.A., "DNA Sequence Diversity in a 9.7–kb Region of the Human Lipoprotein Lipase Gene," *Nature Genetics*, 1998, 223–240.

Nordhoff, E. et al, "Comparison of IR–and UV–Matrix–Assisted Laster Desorption/ionization Mass Spectrometry of Oligodeoxynucleotides," *Nucleic Acids Research*, 1994, 22: No. 13, 2460–2465.

Nordhoff, E. et al, "Ion Stability of Nucleic Acids in Infrared Matrix–Assisted Laser Desorption/ionization Mass Spectrometry," *Nucleic Acids Research*, 1993, 21:No. 15 3347–3357.

Olsen, D.B. et al, "[8] Direct Sequencing of Polymerase Chain Reaction Products," *Methods of Enzymology*, Vol 218 pp 79–92, 1993.

Ono, T., et al., "2'–Floro Modified Nucleic Acids: Polymerase–Directed Synthesis, Properties and Stability to Analysis by Matrix–assisted Laser Desorption/Ionization Mass Spectrometry," *Nucleic Acids Research*, 1997, 25: 4581–4588.

Pedersen et al., "A Method for Directing Evolution and Functional Cloning of Enzymes," *Proc. Natl. Acad. Sci.* USA, 1998, 95:10523–8.

Pieles, U, et al, "Matrix–Assisted Laser Desorption Ionization Time–of–Flight Mass Spectrometry: a Powerful Tool for the Mass and Sequence Analysis of Natural and Modified Oligonucleotides," *Nucleic Acids Research*, 1993, 21:No. 14 3191–3196.

Polesky et al., "Identification of Residues Critical for the Polymerase Activity of the Klenow Fragment of DNA Polymerase I from *Eschericia coli*,*" *J. Biol. Chem.*, 1990, 265:14579–91.

Pomerantz, S.C., et al., "Determination of Oligonucleotide Composition from Mass Spectrometrically Measured Molecular Weight," *J. Am. Soc. Mass Spectrom.*, 1993, 4: 204–209.

Prober, et al, "A System for Rapid DNA Sequencing with Florescent Chain–Terminating Dideoxynucleotides," *Science* 1987, vol. 238, 336–341.

Sanger, et al., "DNA Sequencing with Chain–Terminating Inhibitors," *Proc. Nat. Acad. Sci. USA*, 74, 5463–5467 1977.

Schneider, K. and Chait, B.T., "Increased Stability of Nucleic Acids Containing 7–deaza–quanosine and 7–deaza–adenosine May Enable Rapid DNA Sequencing by Matrix–Assisted Laser Desorption Mass Spectrometry," *Nucleic Acids Research,* 1995, 23: 1570–1575.

Siebenlist, et al., "Contacts Between *Escherichia coli* RNA Polymerase and an Early Promoter of Phase T7," *Proc. Natl. Acad. Sci.* USA, 1980, 77:122.

Siuzdak, G. "The Emergence of Mass Spectrometry in Biochemical Research," *Proc. Natl. Acad. Sci.,* 1994, 91:11290–11297.

Sousa, et al, "A Mutant T7 RNA Polymerase as a DNA Polymerase," *EMBO Journal* vol. 14 No. 18, pp. 4609–4621, 1995.

Stemmer, W. P. C., "Rapid Evolution of a Protein in vitro by DNA Shuffling," *Nature,* 1994, 370:389–391.

Tabor, S., et al., "DNA Sequence Analysis with a Modified Bacteriophage T7 DNA Polymerase," *Proc. Natl. Acad. Sci.* USA, 1987, 84:4767–4771.

Venter, J. C., et al., "Shotgun Sequencing of the Human Genome," *Science,* 1998, 280:1540–1542.

Verdine, et al, "Immobilized Metal Affinity Chromatography of DNA," *Dept. of Chemistry, Harvard University,* May 29, 1996.

Verdine, et al., "Template–Directed Interference Footprinting of Cytosine Contacts in s Protein–DNA Complex: Potent Interference by 5–Aza–2'–deoxycytidine," *Biochemistry,* 1992, 31:11265–11273.

Verdine, et al., "Template–Directed Interference Footprinting of Protein–Adenine Contacts," *JACS,* 1996, 118:6116–6120.

Verdine, et al., "Template–Directed Interference Footprinting of Protein–Guanine Contacts in DNA;" *JACS,* 1991, 113:5104–5106.

Verdine, et al., "Template–Directed Interference Footprinting of Protein–Thymine Contacts," *JACS,* 1993, 115: No. 1 373–374.

Voss, H., et al., "Automated Low–Redundancy Large–Scale DNA Sequencing by Primer Walking," *Biotechniques,* 1993, 15:741–721.

Wang, B. H., et al "Matrix–Assisted Laser Desorption/Ionization Time–of–Flight Mass Spectrometry of Chemically Modified Oligonucleotides," *Analytical Chemical,* 1994, 66: 1918–1924.

Wang, B. H., et al, "Sequencing of Modified Oligonucleotides Using In–Source Fragmentation and Delayed Pulsed Ion Extraction Matrix–Assisted Laser Desorption Ionization Time–of–Flight Mass Spectrometry," *Internat'l J. of Mass Spec. and Ion Process,* 1997, 169/170:331–350.

Weber, J. L. "Human Whole–Genome Shotgun Sequencing," *Genome Research,* 1997, 7:401–409.

Williams, E. R., "Tandem FTMS of Large Biomolecules," *Anal. Chem.,* 1998, 70:179A–185A.

Wu, K., et al., "Time–of–Flight Mass Spectrometry of Underivatized Single–Stranded DNA oligomers by Matrix–Assisted Laser Desorption," *Anal. Chem,* 1994, 66, 1637–1645.

GENOTYPING BY MASS SPECTROMETRIC ANALYSIS OF ALLELIC FRAGMENTS

RELATED APPLICATIONS

This application is a continuation-in-part of U.S. Ser. No. 09/394,467 to Stanton, Wolfe, and Verdine, filed Sep. 10, 1999 now U.S. Pat. No. 6,566,059, entitled "A METHOD FOR ANALYZING POLYNUCLEOTIDES." Ser. No. 09/394,467 in turn claims the benefit of U.S. Provisional Patent Application, serial No. 60/102,724, filed Oct. 1, 1998, and U.S. Provisional Patent Application, serial No. 60/149,533, filed Aug. 17, 1999, both of which are also entitled "A METHOD FOR ANALYZING POLYNUCLEOTIDES." Each of these applications is incorporated by reference in its entirety, including drawings and tables, as if fully set forth herein.

FIELD OF THE INVENTION

The present invention relates generally to organic chemistry, analytical chemistry, biochemistry, molecular biology, genetics, diagnostics and medicine. In particular, it relates to methods for genotyping diploid cells or organisms by comparing the masses of fragments of alleles that include the polymorphic locus.

BACKGROUND OF THE INVENTION

The following is offered as background information only and is not intended nor admitted to be prior art to the present invention.

The ability to detect DNA sequence variances in an organism's genome has become an important tool in the diagnosis of diseases and disorders and in the prediction of response to therapeutic regimes. It is becoming increasingly possible, using early variance detection, to diagnose and treat, even prevent the occurrence of, a disease or disorder before it has physically manifested itself. Furthermore, variance detection can be a valuable research tool in that it may lead to the discovery of genetic bases for disorders the cause of which were hitherto unknown or thought to be other than genetic.

The most common type of sequence variance is the single nucleotide polymorphism or SNP. As the name suggests, a SNP involves the substitution of one nucleotide to another at a particular locus in a gene. While each SNP involves but one nucleotide, a single gene may contain numerous SNPs.

It is estimated that SNPs occur in human DNA at a frequency of about 1 in 100 nucleotides when 50 to 100 individuals are compared. Nickerson, D. A., *Nature Genetics*, 1998, 223–240. This translates to as many as 30 million SNPs in the human genome. However, very few SNPs have any effect on the physical well-being of humans. Detecting the 30 million SNPs and then determining which of them are relevant to human health will clearly be a formidable task.

Complete DNA sequencing is presently the definitive procedure for detecting sequence differences. However, current DNA sequencing technology is costly, time consuming and, in order to assure accuracy, highly redundant. Most sequencing projects require a 5- to 10-fold coverage of each nucleotide to achieve an acceptable error rate of 1 in 2,000 to 1 in 10,000 bases. In addition, DNA sequencing is an inefficient way to detect SNPs. While on the average a SNP occurs once in about every 100 nucleotides, when variance between two copies of a gene, for example those associated with two chromosomes, is being compared, a SNP may occur as infrequently as once in 1,000 or more bases. Thus, only a small segment of the gene in the vicinity of the SNP locus is really of interest. If full sequencing is employed, a tremendous number of nucleotides will have to be sequenced before any useful information is obtained. For example, to compare ten versions of a 3,000 nucleotide DNA sequence for the purpose of detecting four variances among them, even if only 2-fold redundancy is employed (each strand of the double-stranded 3,000 nucleotide DNA segment from each individual is sequenced once), 60,000 nucleotides would have to be sequenced (10×3,000×2). Furthermore, sequencing problems are often encountered that can require even more runs, often with new primers. Thus, as many as 100,000 nucleotides might have to be sequenced to detect four variances.

Determination of whether a particular gene of a species or of an individual of that species contains a SNP is called genotyping. Complete sequencing is, therefore, a method for accomplishing genotyping but, as is indicated above, it is slow, costly and extremely inefficient.

An alternative to complete sequencing to compare the masses of fragments of two alleles of a gene known or suspected to contain a SNP. A mass difference between any of the fragments indicates that the alleles contained different nucleotides in the divergent fragments which, in turn, reveals that the alleles are heterozygous. Generally, the procedure involves amplifying a segment of each allele using a modified nucleotide corresponding to one of the natural nucleotides involved in the polymorphism, which modified nucleotide imparts enhanced susceptibility to cleavage at its sites of incorporation. The modified nucleotide is incorporated into the amplicon in at least a portion of the points of occurrence of the natural nucleotide. The modified segments are then cleaved at the sites of incorporation of the modified nucleotide to give two sets of fragments, which are compared as indicated above. While providing a vast improvement in terms of speed, efficiency and cost over complete sequencing, this procedure is not free of potential shortcomings.

For example, large differences in assay signals between thermocyclers can limit the robustness of the procedure. A relatively high occurrence (as much as 25%) of allele-specific reactions in which only one diagnostic product is produced from a heterozygous mixture may confound the result. An amplification bias for the allele that has the site of incorporation of the modified nucleotide farthest from the extending primer terminus (called skewing) may occur. In addition, automated calling of genotype may be affected by the exponential decrease in mass spectometric signal with linear increases in fragment size. Heterozygotes that give fragments differing in size by 5–10 nucleotides can produce peaks of very unequal intensity that are difficult for automated devices to recognize.

What is needed, then, is a method that retains the rapid, inexpensive, efficient, yet accurate characteristics of the mass comparison technique but which eliminates the above potential shortcomings. The present invention provides such a method.

SUMMARY OF THE INVENTION

Thus in one aspect the present invention relates to a method for genotyping a diploid organism. The method comprises taking two alleles of a target gene of a diploid organism suspected to contain a polymorphism and obtaining a segment of each that contains the suspected polymorphic locus. A natural nucleotide is replaced at greater than 90% of its points of occurrence in the two segments with a modified nucleotide to give two modified segments. In doing so, the natural nucleotide that is replaced is not a nucleotide involved in the polymorphism. Furthermore, replacing the natural nucleotide with a modified nucleotide comprises amplification using a primer that hybridizes to each segment such that, after amplification, a first modified nucleotide is incorporated between the end of the primer and the polymorphic locus and a second modified nucleotide is located from 5 to 20 nucleotides downstream from the first modified nucleotide. The modified segments are then cleaved at greater than 90% of the points of occurrence of the modified nucleotide to give two sets of fragments each of which includes a 5–20 nucleotide fragment. The masses of the 5–20 nucleotide fragments from the two modified segments are then compared to detect the presence or absence of the polymorphism.

In an aspect of this invention, the second modified nucleotide is from 7 to 20 nucleotides downstream of the first modified nucleotide and it is these 7–20 20 nucleotide fragments that are compared to detect the presence or absence of the polymorphism.

In as aspect of this invention, the second modified nucleotide is from 7 to 12 nucleotides downstream of the first modified nucleotide and it is these 7–12 nucleotide fragments that are compared to detect the presence or absence of the polymorphism.

In an aspect of this invention, if there would be less than 5 nucleotides between the first and second modified nucleotides, the method further comprises using a primer that contains a point mutation that removes the site of incorporation of one of the modified nucleotides.

In an aspect of this invention, if there are less than 7 nucleotides between the first and the second modified nucleotides, the method further comprises using a primer that contains a point mutation that removes the site of incorporation of one of the modified nucleotides.

In an aspect of this invention, if there would be more than 20 nucleotides between the first and second modified nucleotides, the method further comprises a primer, which contains a point mutation that incorporates a modified nucleotide downstream of the first modified nucleotide or upstream of the second modified nucleotide.

In an aspect of this invention, if there would be more than 12 nucleotides between the first and the second modified nucleotides, the method further comprises a primer, which contains a point mutation that incorporates a modified nucleotide downstream of the first modified nucleotide or upstream of the second modified nucleotide.

An aspect of this invention is a method for genotyping a diploid organism, comprising, first, providing two alleles of a target gene of a diploid organism suspected to contain a polymorphism and then obtaining a segment from each allele wherein the segment contains the suspected polymorphic locus. A natural nucleotide in the segment is then replaced at greater than 90% of its points of occurrence in the two segments with a modified nucleotide to give a first and a second modified segment. IN this aspect of the invention, the natural nucleotide that is replaced is a nucleotide involved in the polymorphism. Replacing the natural nucleotide with a modified nucleotide comprises amplification using a primer that hybridizes to each segment such that, after amplification, the suspected polymorphic locus is the first site of incorporation of a modified nucleotide after the end of the primer. Furthermore a second modified nucleotide must be located from 5 to 20 nucleotides downstream of the first modified nucleotide. The first and second modified segments are cleaved at greater than 90% of the points of occurrence of the modified nucleotide to give a first and second set of fragments. Finally, the masses of the two sets of fragments are compared for the presence of the 5–20 nucleotide fragment wherein, if the fragment is present or absent in both sets, the gene is homozygous and if the fragment is present in only one set, the gene is heterozygous.

In an aspect of this invention, a nucleotide known to be involved in the polymorphism is replaced with a mass-modified nucleotide.

In an aspect of this invention, comparing the masses of the fragments comprises using a mass spectrometer.

In an aspect of this invention, the mass spectrometer is a MALDI mass spectrometer.

In an aspect of this invention, the MALDI mass spectrometer is a MALDI-TOF mass spectrometer.

In an aspect of this invention, the mass spectrometer is an ESI mass spectrometer.

In an aspect of this invention, the percentage replacement of a natural nucleotide with a modified nucleotide, the percentage cleavage at a modified nucleotide, or both the percentage replacement and the percentage cleavage, is greater than 95%.

In as aspect of this invention, the percentage replacement of a natural nucleotide with a modified nucleotide, the percentage cleavage at a modified nucleotide, or both the percentage replacement and the percentage cleavage, is greater than 99%.

DETAILED DESCRIPTION OF THE INVENTION

BRIEF DESCRIPTION OF THE FIGURES

The figures herein are provided for the sole purpose of illustrating certain embodiments of this invention. They are not intended, nor are they to be construed, as limiting the scope of this invention in any manner whatsoever.

DEFINITIONS

As used herein, a "gene" refers to the basic unit of heredity that carries the code for every physical trait that distinguishes an individual of a species.

As used herein, "genotyping" refers to the process of determining the single nucleotide polymorphisms (SNPs) present in the genes of a species or of an individual of that species.

As used herein, "diploid" refers to an organism in which each gene has two alleles, one on each chromosome of a homologous pair.

As used herein, an "organism" refers to any living entity comprised of eukaryotic cells. This includes plants, reptiles, fish, birds, animals and, in particular, human beings.

As used herein, an "allele" refers to an alternative form of a gene. More specifically, an allele is one of two or more different versions of a gene that can occupy the same position or locus on a chromosome. If the same allele occupies the position on both chromosomes of a diploid pair, that DNA, cell or individual is said to be "homozygous." In, on the other hand, the alleles occupying the same locus on the two chromosomes are different, the DNA, cell or individual is said to be "heterozygous."

As used herein, a "reagent" refers to a chemical entity or physical force that cleaves a modified segment at the site of incorporation of a modified nucleotide. Such reagents include, without limitation, a chemical or combination of chemicals, normal or coherent (laser) visible or uv light, heat, high energy ion bombardment and irradiation. A "reagent" can refer to a single chemical entity or physical force, a combination of two or more chemical entities or physical forces or a combination of chemical entities and physical forces. If more than one chemical entity or physical force is used, they can be applied simultaneously or sequentially. By simultaneously is meant that two or more reagents are placed in the reaction mixture at the same time with a segment to be cleaved. It is understood that, once placed together in the reaction mixture, one of the reagents may in fact react with the segment before the other one. By sequentially is meant that a segment to be cleaved are first placed in contact with one reagent and only after that reagent has performed is the reaction product of the first reaction placed in contact with the second reagent, etc.

As used herein, a "single nucleotide polymorphism" or "SNP" refers to polynucleotide that differs from another polynucleotide at a particular locus by virtue of a single nucleotide exchange. A polynucleotide may, of course, contain numerous SNPs; however, each must occur at a different locus. For example, exchanging one A for one C, G or T at a particular locus in the sequence of a polynucleotide constitutes a SNP. When referring to SNPs, the polynucleotide is most often genetic DNA. SNPs can occur in coding and non-coding regions of the gene. Those in coding regions are of primary interest because it is they that can cause changes in the phenotype, i.e., an detectable physical difference in an individual compared to the general population. Detectable physical differences include, without limitation, a difference in susceptibility to a particular disease or disorder or a difference in response to a therapeutic regime used to treat or prevent a disease or disorder.

As used herein, a "polymorphic locus" refers to a location in the nucleotide sequence of the alleles of a gene of a diploid organism that may be occupied by different nucleotides. The difference may be the result of a SNP, a point mutation, a nucleotide insertion or a nucleotide deletion.

As used herein, a "suspected" polymorphic locus refers to a site in the alleles of a gene where a polymorphism is generally known to occur but it is unknown if the alleles of that gene in the single specific organism being examined contain the polymorphism.

As used herein, "amplifying" or "amplification" refers to the process of producing multiple copies of a segment of a double stranded polynucleotide by hybridizing natural nucleotide primers 5' to the segment to be amplified and then using a polymerase or polymerases to extend the primer to reproduce the sequences of the strands. A common amplification technique is PCR, the well-known polymerase chain reaction, which results in a logarithmic increase in the number of copies of the segment being amplified. The end result of amplification is the production of a sufficient amount of the segments to permit relatively facile manipulation. Manipulation refers to both physical and chemical manipulation, that is, the ability to move bulk quantities of the segments around and to conduct chemical reactions with them that result in detectable products.

As used herein, "downstream" means in the direction away from the 3' end of a primer, that is, in the direction of extension and "upsteam" means in a direction toward the 3' end of a primer or counter to the direction of extension.

As used herein, a "point mutation" refers to a change at a single locus in a polynucleotide strand. The change may be the deletion of a nucleotide, the addition of a nucleotide or the substitution of one nucleotide for another.

As used herein a "segment" of an allele refers to a portion of the complete nucleotide sequence of the allele.

As used herein a "modified segment" refers to a segment in which a natural nucleotide has been replaced at greater than 90%, preferably greater than 95%, most preferably greater than 99% of its points of occurrence in the segment with a modified nucleotide. For the purposes of this disclosure, the phrase "at substantially each point of occurrence" will be used as a short-hand for the preceding list of increasing preferences.

As used herein, to "contain" a suspected polymorphic locus means that the SNP site is contained in the nucleotide sequence of the amplified segments.

By "homozygous" is meant that the two alleles of a diploid cell or organism have exactly the same nucleotide sequence.

By "heterozygous" is meant that the two alleles of a diploid cell or organism have a difference in their nucleotide sequence at a particular locus. In most cases, the difference is a SNP, although it may be a mutation, an insertion or a deletion.

A "sequence" or "nucleotide sequence" refers to the order of nucleotide residues in a nucleic acid.

A "nucleoside" refers to a base covalently bonded to a sugar moiety. The base may be adenine (A), guanine (G) (or its substitute, inosine (I)), cytosine (C), or thymine (T) (or its substitute, uracil (U)). The sugar may be ribose (the sugar of a natural nucleotide in RNA) or 2-deoxyribose (the sugar of a natural nucleotide in DNA).

A "nucleoside triphosphate" refers to a nucleoside linked to a triphosphate group $(O^-\text{---}P(=O)(O^-)\text{---}O\text{---}P(=O)(O^-)\text{---}O\text{---}P(=O)(O^-)\text{---}O\text{---}nucleoside)$. The triphosphate group has four formal negative charges that require counter-ions, i.e., positively charged ions. Any positively charged ion can be used, e.g., without limitation, $Na^+$, $K^+$, $NH_4^+$, $Mg^{2+}$, $Ca^{2+}$, etc. $Mg^{2+}$ is one of the most commonly used counter-ions. It is accepted convention in the art to omit the counter-ion, which is understood to be present, when displaying nucleoside triphosphates; the convention is followed in this application.

As used herein, unless expressly noted otherwise, the term "nucleoside triphosphate" or reference to any specific nucleoside triphosphate; e.g., adenosine triphosphate, guanosine triphosphate or cytidine triphosphate, refers to the triphosphate made using either a ribonucleoside or a 2'-deoxyribonucleoside.

A "nucleotide" refers to a nucleoside linked to a single phosphate group.

A "natural nucleotide" refers to an A, C, G or U nucleotide when referring to RNA and to dA, dC, dG and dT (the "d" referring to the fact that the sugar is deoxyribose) when referring to DNA. A natural nucleotide also refers to a nucleotide which may have a different structure from the above, but which is naturally incorporated into a polynucleotide sequence by the organism which is the source of the polynucleotide.

As used herein, a "modified nucleotide" refers to a nucleotide that meets two criteria. First, a modified nucleotide is a "non-natural" nucleotide. In one aspect, a "non-natural" nucleotide may be a natural nucleotide that is placed in non-natural surroundings. For example, in a polynucleotide that is naturally composed of deoxyribonucleotides, i.e., DNA, a ribonucleotide would constitute a "non-natural" nucleotide. Similarly, in a polynucleotide that is naturally composed of ribonucleotides, i.e., RNA, a deoxyribonucleotide would constitute a non-natural nucleotide. A "non-natural" nucleotide also refers to a natural nucleotide that has been chemically altered. For example, without limitation, one or more substituent groups may be added to the base, sugar or phosphate moieties of the nucleotide. Or, one or more substituents may be deleted from the base, sugar or phosphate moiety. Finally, one or more atoms or substituents may be substituted for one or more other atoms or substituents in the nucleotide. A "modified" nucleotide may also be a molecule that resembles a natural nucleotide little, if at all, but is nevertheless capable of being incorporated by a polymerase into a polynucleotide in place of a natural nucleotide.

The second criterion associated with a "modified" nucleotide, as the term is used herein, is that it alters the cleavage properties of the polynucleotide into which it is incorporated. For example, without limitation, incorporation of a ribonucleotide into a polynucleotide composed predominantly of deoxyribonucleotides imparts a heightened susceptibility to alkaline cleavage at the site of incorporation that does not otherwise exist. This second criterion of a "modified" nucleotide may be met by a single non-natural nucleotide substitution (e.g., the substitution of a ribonucleotide for a deoxyribonucleotide described above). It may also be met by substitution of two or more non-natural nucleotides that do not individually alter the cleavage properties of a polynucleotide but, rather, when in a particular spatial relationship with one another, result in cleavage of the polynucleotide (referred to as "dinucleotide cleavage").

As used herein, "having different cleavage characteristics" refers to two or more modified nucleotides that, when incorporated into a polynucleotide, can be selectively cleaved in each other's presence by using different reagents and/or reaction conditions.

"Replacing" a natural nucleotide with a modified nucleotide refers to the process of amplifying a segment using one modified nucleotide and the three remaining natural nucleotides such that the natural nucleotide corresponding to the modified nucleotide is replaced at substantially each point of occurrence in the segment by the modified nucleotide. As used herein, "replacing" may also refer to the process of amplifying a segment using two modified nucleotides and the two remaining natural nucleotides simultaneously such that each natural nucleotide is replaced as substantially each point of occurrence in the segment by its corresponding modified nucleotide.

"Cleaving" a modified segment refers to the process of contacting the segment with a reagent that selectively severs the nucleotide chain at substantially each point of occurrence of a modified nucleotide.

A "polynucleotide" refers to a linear chain of 30 or more nucleoside 5'-monophosphate residues linked by phosphodiester bonds between the 3' hydroxyl group of one sugar and the 5' hydroxyl group of the next.

A "modified polynucleotide" refers to a polynucleotide in which a natural nucleotide has been replaced at substantially each point of its occurrence with a modified nucleotide. It may also refer to the replacement of two, three or four natural nucleotides with two, three or four modified nucleotides where each of the modified nucleotides alters the cleavage properties of the resulting modified polynucleotide differently. Cleavage can then be selectively carried out with each modified nucleotide in the presence of the others.

As used herein, to "alter the cleavage properties" of a polynucleotide means to render the polynucleotide more or less susceptible to cleavage at the point of incorporation of a modified nucleotide than it would be with a natural nucleotide or a different non-natural nucleotide at the same locus. It is presently preferred to "alter the cleavage properties" by rendering a polynucleotide more susceptible to cleavage at the site of incorporation of a modified nucleotide than at any other locus in the molecule. As used herein, the use of the singular when referring to nucleotide substitution or cleavage is to be construed as including substitution or cleavage at substantially each point of occurrence of a modified nucleotide unless expressly stated otherwise.

As used herein, a "template" refers to a polynucleotide strand, which a polymerase uses as a means of recognizing which nucleotide it should next incorporate into a growing strand to duplicate a polynucleotide. If the polynucleotide is DNA, it may be single-stranded or double-stranded. When employing the polymerase chain reaction (PCR) to amplify a template using the methods of this invention, the copies made contain modified nucleotides. These modified segments are still capable of serving as templates for the production of further copies of identically modified amplicons.

As used herein, a "primer" refers to an oligonucleotide formed from natural nucleotides, the sequence of which is complementary to a segment of a template to be replicated. A polymerase uses the primer as the starting point for the replication process. By "complementary" is meant that the nucleotide sequence of a primer is such that it will hybridize to the template by formation of hydrogen bonded base-pairs over a length of at least ten consecutive bases. In the methods of this invention, a primer is never modified by replacement of a natural nucleotide with a modified nucleotide nor does cleavage ever occur in the nucleotide sequence of the primer.

As used herein, a "polymerase" refers, without limitation, to DNA or RNA polymerases, mutant versions thereof and to reverse transcriptases. DNA or RNA polymerases can be mutagenized by, without limitation, nucleotide addition, nucleotide deletion, one or more point mutations, "DNA shuffling" or joining portions of different polymerases to make chimeric polymerases. Combinations of these mutagenizing techniques may also be used. A polymerase catalyzes the assembly of nucleotides to form polynucleotides. Polymerases may be used either to extend a primer once or repetitively. Repetitive extension is sometimes referred to as amplification. Amplification may be accomplished by, without limitation, PCR, NASBR, SDA (Strand Displacement Amplification), 3SR (Self-Sustained Sequence Replication Reaction), TSA (Tyramide Signal Amplification) and rolling circle replication. In the methods of this invention, one or more polymerases and one or more extension or amplification techniques may be used to replicate a particular polynucleotide.

As used herein, a "chemical oxidant" refers to a reagent capable of increasing the oxidation state of a group on a molecule. For instance, without limitation, a hydroxyl group (—OH) can be oxidized to an aldehyde, ketone or acid. Some examples of chemical oxidants are, without limitation, potassium permanganate, t-butyl hypochlorite, m-chloroperbenzoic acid, hydrogen peroxide, sodium hypochlorite, ozone, peracetic acid, potassium persulfate, and sodium hypobromite.

As used herein, a "chemical base" refers to a chemical compound that, in aqueous medium, has a pK greater than 7.0. A chemical base may be inorganic or organic. Examples of inorganic chemical bases include, without limitation, alkali (sodium, potassium, lithium) and alkaline earth (calcium, magnesium, barium) hydroxides, carbonates, bicarbonates, phosphates and the like. Ammonium hydroxide is another inorganic chemical base. Nitrogen-containing organic compounds such as pyridine, aniline, quinoline, morpholine, piperidine and pyrrole are also chemical bases. Nitrogen-containing chemical bases may be primary (the nitrogen has two hydrogen atoms and one other substituent on it), secondary (the nitrogen has one hydrogen and two other substituents on it) or tertiary (the nitrogen has no hydrogen atoms on it). Chemical bases may be used as aqueous solutions, which may be mild (usually due to dilution) or strong (concentrated solutions). A chemical base also refers to a strong non-aqueous organic base; examples include, without limitation, sodium methoxide, sodium ethoxide and potassium t-butoxide.

Secondary amines are presently preferred chemical bases for use in the cleavage of modified nucleotides. Secondary amines useful in the methods of this invention include, without limitation, pyrrolidine, piperidine, 3-pyrrolidinol, 2-pyrrolidinemethanol, 3-pyrrolidinemethanol, 4-hydroxypiperidine, 4-(2-hydroxyethyl)piperidine, hexamethyleneimine, heptamethyleneimine, diethylamine, diproylamine, dibutylamine, proline, morpholine, piperizine, picolinic acid, piperazine-2-carboxylic acid, 4-piperidineethanol and isopecotic acid. A secondary amine useful in the methods herein may also be polymer bound, for example, without limitation, piperidine-4-carboxylic acid polymine resin (polystyrene).

As used herein, the term "acid" refers to a substance that dissociates in water to produce one or more hydrogen ions. An acid may be inorganic or organic. It may be a strong acid, which generally infers highly concentrated, or mild, which generally infers dilute. It is, of course, understood that acids inherently have different strengths; e.g., sulfuric acid is much stronger than acetic acid. The proper choice of acid will be apparent to those skilled in the art from the disclosures herein. Preferably, the acids used in the methods of this invention are mild. Examples of mild inorganic acids are, without limitation, dilute hydrochloric acid, dilute sulfuric acid, dilute nitric acid, phosphoric acid and boric acid. Examples, without limitation, of mild organic acids are formic acid, acetic acid, benzoic acid, p-toluenesulfonic acid, trifluoracetic acid, naphthoic acid, uric acid and phenol.

As used herein, "bond," "bonding" or "bonded" refers, unless otherwise expressly stated, to covalent bonds between the entities which are the subject of the bonding.

As used herein, a "functional group" refers, without limitation, to an entity such as amino (—$NH_2$), hydroxyl (—OH), cyano (—C≡N), nitro ($NO_2$), carboxyl (—COOH), acid halide (C(O)X, wherein X is chloro or bromo), ester (—C(O)OR, R is methyl ethyl, etc.), formyl (—CHO), keto (—$CH_2$C(O)$CH_2$—), alkenyl (—C=C—), alkynyl (—C≡C—), halo (F, Cl, Br and I) groups and the like, which are capable of reacting with other functional groups to form bridges of covalently bonded atoms linking together the entities to which the functional groups were initially bonded. For instance, an amino functional group can react with an acid halide functional group to form an amide (—C(O)$NH_2$). Likewise, a hydroxyl group can react with an acid halide to form an ester. Many such functional groups are known to those skilled in the art. The use of any of them in the methods herein to link modified nucleotides to fluorescent tags.

"Hybridizing" or "hybridization" refers to the formation of A-T or C-G base pairs among a string of contiguous nucleotides in an oligonucleotide or polynucleotide (usually at least 10 to form a stable hybridization product). In the present case, the oligonucleotides are a primer and a template or a primer and an immobilization oligonucleotide. To hybridize, the primer and template or primer and oligonucleotide must be "complementary" in the region of base-pair formation. "Complementary" means that the locus of each A, C, G and T (or U, if the oligonucleotide or template comprises ribonucleotides) in the sequence of the hybridizing portion of the primer corresponds to a T, G, C or A, respectively, in the same locus of the sequence of the template or oligonucleotide.

"Mass spectrometry" refers to a technique for mass analysis known in the art which includes, but is not limited to, matrix assisted laser desorption ionization (MALDI) and electrospray ionization (ESI) mass spectrometry optionally employing, without limitation, time-of-flight, quadrupole or Fourier transform detection techniques. While the use of mass spectrometry constitutes a preferred embodiment of this invention, it will be apparent that other instrumental techniques are, or may become, available for the determination of the mass or the comparison of masses of oligonucleotides. An aspect of the present invention is the determination and comparison of masses and any such instrumental procedure capable of such determination and comparison is deemed to be within the scope and spirit of this invention.

As used herein, the terms "selective," "selectively," "substantially," "essentially," "uniformly" and the like, mean that the indicated event occurs to a particular degree. For example, the percent incorporation of a modified nucleotide herein is characterized as "substantially complete." As used herein, this means greater than 90%, preferably greater than 95% and, most preferably, greater than 99%. With regard to cleavage at a modified nucleotide, "selectively" means greater than 10 times, preferably greater than 25 times, most preferably greater than 100 times that of the natural nucleotide in the modified polynucleotide. The percent cleavage at a modified nucleotide is also referred to herein as being "substantially complete." This means greater than 90%, preferably greater than 95%, most preferably greater than 99% complete.

Discussion

The methods of this invention can be used to examine the genetic DNA of an individual displaying symptoms of a particular disease or disorder known or suspected to be genetically based. Comparison of the DNA of the individual with that of healthy members of the same population will confirm whether the individual is afflicted with a particular genetically-related disease or disorder. Conversely, the method can be used to study an individual displaying symptoms of a disease or disorder of unknown origin to determine if it has a genetic component.

Of course, the methods herein are not limited to the examination of the genetic aspects of diseases and disorders of human beings. For example, without limitation, plants have genetic variations that affect such traits as disease resistance, temperature accommodation, drought resistance, product size, crop yield, flavor, etc. Animals likewise have genetic variations that affect size, fertility, growth rate, disease resistance, body composition and the like. Knowing which genetic variations are responsible for these and may other beneficial characteristics can have significant economic impact. The methods of this invention are equally applicable to these areas of genetic inquiry.

Nucleotide Modification and Cleavage

A modified nucleotide may contain a modified base, a modified sugar, a modified phosphate ester linkage or any combination of these. With regard to the present invention, the presently preferred modified nucleotide is a base-modified nucleotide.

Base-modified Nucleotides

Base-modified nucleotide refers to the chemical modification of the adenine, cytosine, guanine or thymine (or, in the case of RNA, uracil) moiety of a nucleotide. The resulting modified nucleotide is more susceptible to cleavage than the natural nucleotides in the polynucleotide. The following are examples, without limitation, of base modification. Other modifications of bases will become apparent to those skilled in the art based on the disclosures herein. Such base modifications are within the scope of this invention.

1. Adenine (1) can be replaced with 7-deaza-7-nitroadenine (2). 7-Deaza-7-nitroadenine is readily incorporated into polynucleotides by various polymerases. The 7-nitro group activates C-8 to attack by chemical base such as, without limitation, aqueous sodium hydroxide or aqueous piperidine, which results in strand scission. Verdine, et al., *JACS*, 1996, 118:6116–6120;

When the cleavage reaction is carried out in the presence of a phosphine, for example, without limitation, tris(2-carboxyethyl) phosphine (TCEP) and a base, complete cleavage is obtained. Thus, when DNA modified by incorporation of 7-nitro-7-deaza-2'-deoxyadenosine was treated with 0.2 M TCEP/1 M piperidine/0.5 M Tris base at 95° C. for one hour, complete cleavage was observed on denaturing polyacrylamide gel (20%) electrophoresis. Other bases such as, without limitation, ammonium hydroxide can be used in place of piperidine and Tris base. This procedure, i.e., the use of a phosphine in conjunction with a base, should work for any base-modified nucleotide in which the modified adenine, cytosine, guanine, thymine or uracil is labile to chemical base.

Secondary amines are presently preferred chemical bases for use in cleavage reactions of this invention. Some representative secondary amines useful in cleavage reactions of this invention include, without limitation, diethylamine, dipropylamine and pyrrolidine. However, secondary amines having a boiling point above 100° C. at atmospheric pressure are preferred. While not being bound to any particular theory, this might be due to the fact that lower boiling secondary amines are volatilized at the temperatures used for cleavage, 90° C. or higher, making it difficult to maintain an optimal concentration of the amine in the cleavage reaction. Examples of higher boiling secondary amines include, without limitation, dibutylamine, piperidine, 3-pyrrolidinol, hexamethyleneimine, morpholine and pyrazine. Secondary amines having a boiling point above 150° C. are even more preferable, with those having a boiling point above 200° C. being the presently most preferred. Such high boiling secondary amines include, without limitation, heptamethyleneimine, 3-pyrrolidinol, 2-pyrrolidinemethanol, 3-pyrrolidinemethanol, proline, picolinic acid, piperazine-2-carboxylic acid, 4-piperidineethanol, isonipecotic acid and piperidine-4-carboxlic acid polymine resin (polystyrene). 3-Pyrrolidinol, 2-pyrrolidinemethanol, 3-pyrrolidinemethanol and piperidine-4-ethanol (4-(2-hydroxyethyl)piperidine) are presently preferred high boiling secondary amines for use in the methods of this invention.

When the cleavage reaction is carried out in the presence of a phosphine and a base, a unique adduct forms. For example, when the phosphine is, without limitation, tris(2-carboxyethyl) phosphine (TCEP), mass spectrometry of the product is consistent with a structure having a ribose-TCEP adduct at its 3' end and a phosphate moiety at its 5' end:

The mechanism of formation of the phosphine adduct is not presently known; however, without being held to any particular theory, the following is a possibility:

The incorporation of a phosphine into the cleavage product can be used to label polynucleotide fragments at the same time cleavage is being performed. By using a phosphine that contains a label or tag but is still capable of forming the above-described adduct, such entities as, without limitation, mass tags, fluorescence tags, radioactive tags and ion-trap tags can be incorporated directly into polynucleotide fragments during cleavage.

While other phosphines useful in the cleavage procedure described above will become apparent to those skilled in the art based on the disclosures herein, and therefore are within the scope of this invention, TCEP is presently preferred. The carboxy (—C(O)OH) groups of TCEP can be readily modified, for example, without limitation, by reaction with an amine, alcohol or mercaptan to form an amide, ester or mercaptoester:

-continued bismodified derivative

In the above scheme, $M^1$ and $M^2$ are independently oxygen, —NH, $NR^1$ or sulfur. $R^1$ and $R^2$ are independently mass, fluorescent, radioactive or ion trap tags.

When a carboxy group is reacted with a carbodiimide in the absence of a nucleophile, the product rearranges to form an N-acylurea. If the carbodiimide contains a fluorophore, the phosphine will then carry it:

Amino group-containing fluorophores such as fluoresceinyl glycine amide, (5-aminoacetamido)fluorescein, 7-amino-4-methylcoumarin, 2-aminoacridone, 5-aminofluorescein, 1-pyrenemethylamine and 5-aminoeosin may also be used to prepare labeled phosphines. Amino derivatives of Lucifer Yellow and Cascade Blue can also be employed as can amino derivatives of biotin. In addition, hydrazine derivatives such as rhodamine and Texas Red hydrazine may be useful in this method.

Fluorescent diazoalkanes, such as, without limitation, 1-pyrenyldiazomethane, may be used to form esters with TCEP. Fluorescent alkyl halides may also react with the carboxylate anion (—C(O)O⁻) of the phosphine to form esters. Such halides include, without limitation, panacyl bromide, 3-bromoacetyl-7-diethylaminocoumarin, 6-bromoacetyl-2-diethylaminonaphthalene, 5-bromomethylfluorescein, BODIPY® 493/503 methyl bromide, monobromobimanes and iodoacetamides such as coumarin iodoacetamide. Naphthalimide sulfonate ester reacts rapidly with the anions of carboxylic acids in acetonitrile to give adducts which are detectable by absorption at 259 nm down to 100 femtomoles and by fluorescence at 394 nm down to four femtomoles.

There are also many amine-reactive fluorescent probes known in the art. TCEP is readily converted into a primary amine and reacted with these entities:

Cytosine (4) can be replaced with 5-azacytosine (5). 5-Azacytosine can be incorporated into polynucleotides by polymerases. 5-Azacytosine is susceptible to cleavage by chemical base, particularly aqueous base such as aqueous piperidine or aqueous sodium hydroxide. Verdine, et al., *Biochemistry*, 1992, 31:11265–1123

4

-continued

5

3. Guanine (6) can be replaced with 7-methylguanine (7) and can likewise be readily incorporated into polynucleotides by polymerases (Verdine, et al., *JACS*, 1991, 113:5104–5106). The resulting nucleotide is susceptible to attack by chemical base, such as, without limitation, aqueous piperidine (Siebenlist, et al., *Proc. Natl. Acad. Sci. USA*, 1980, 77:122).

6

7

4. Either thymine (9) or uracil (10) may be replaced with 5-hydroxyuracil (11) (Verdine, *JACS*, 1991, 113:5104) or 5-aminouracil (12). As with the above-modified bases, these nucleotides can be incorporated into a polynucleotide by enzyme-catalyzed polymerization. While not absolutely necessary, in a presently preferred embodiment, cleavage of 5-hydroxyuracil is accomplished by first treating it with an oxidizing agent, for instance, aqueous permanganate, and then with a chemical base such as aqueous piperidine, as shown.

5. Pyrimidines substituted at the 5-position with an electron withdrawing group such as, without limitation, nitro, halo or cyano, should be susceptible to nucleophilic attack at the 6-position followed by base-catalyzed ring opening and subsequent degradation of the phosphate linkage. An example, which is not to be construed as limiting the scope of this invention in any manner, using 5-substituted cytidine is shown below. If the cleavage is carried out in the presence of tris(carboxyethyl)phosphine (TCEP), adduct 10 may be obtained. The TCEP may be functionalized with a fluorophore as discussed above.

Genotyping

As DNA sequence data accumulates for various species, particularly humans, more and more variances in the genetic code for individuals compared to the general population within a species are being recognized. Some of these variances are being related to phenotypic differences such as an increased susceptibility to a particular disease or a different reaction to a given therapeutic regime. Thus, there is increasing demand for automated, accurate, high throughput, inexpensive methods for determining the status of a specific nucleotide or nucleotides in individuals where variation has been discovered. This procedure—the determination of the nucleotide at a particular location in a DNA sequence—is referred to as genotyping. The methods of this invention are eminently suitable to genotyping.

First, both alleles of a gene that is known to have a polymorphic site are obtained. Then a segment of each allele that contains the polymorphic locus is amplified using a modified nucleotide to replace a natural nucleotide at greater than 90% of the points of its occurrence in the segment. Preferably, replacement occurs at greater than 95% and, most preferably, greater than 99% of the points of occurrence of the natural nucleotide. Amplification by PCR is presently preferred.

In a presently preferred embodiment of this invention, the natural nucleotide that is replaced is not one that is involved in the suspected polymorphism. Thus, if the gene is known to involve an A/T SNP, then the modified nucleotide would be a modified C or G, etc. The modified nucleotide renders the amplified segments more susceptible to cleavage at its sites of incorporation than elsewhere in the segments.

Which natural nucleotide is replaced with a modified nucleotide is determined by examination of the sequence of the segments containing the polymorphic site. First, a nucleotide is selected such that, when it is replaced with a modified nucleotide, a modified nucleotide will be located between the end of the primer and the SNP so that a cleavage site is generated between the primer and the SNP. This eliminates the potential problem discussed previously regarding amplification bias since the site of the first modified nucleotide will be the same in each allele.

In addition, the nucleotide is selected such that, after cleavage of the modified segment, a fragment will be generated that is from 5–20 nucleotides long and contains the polymorphic locus. In a presently preferred embodiment, the length of the fragment will be from 7–12 nucleotides. This is exemplified in FIG. 1.

Figure 1:
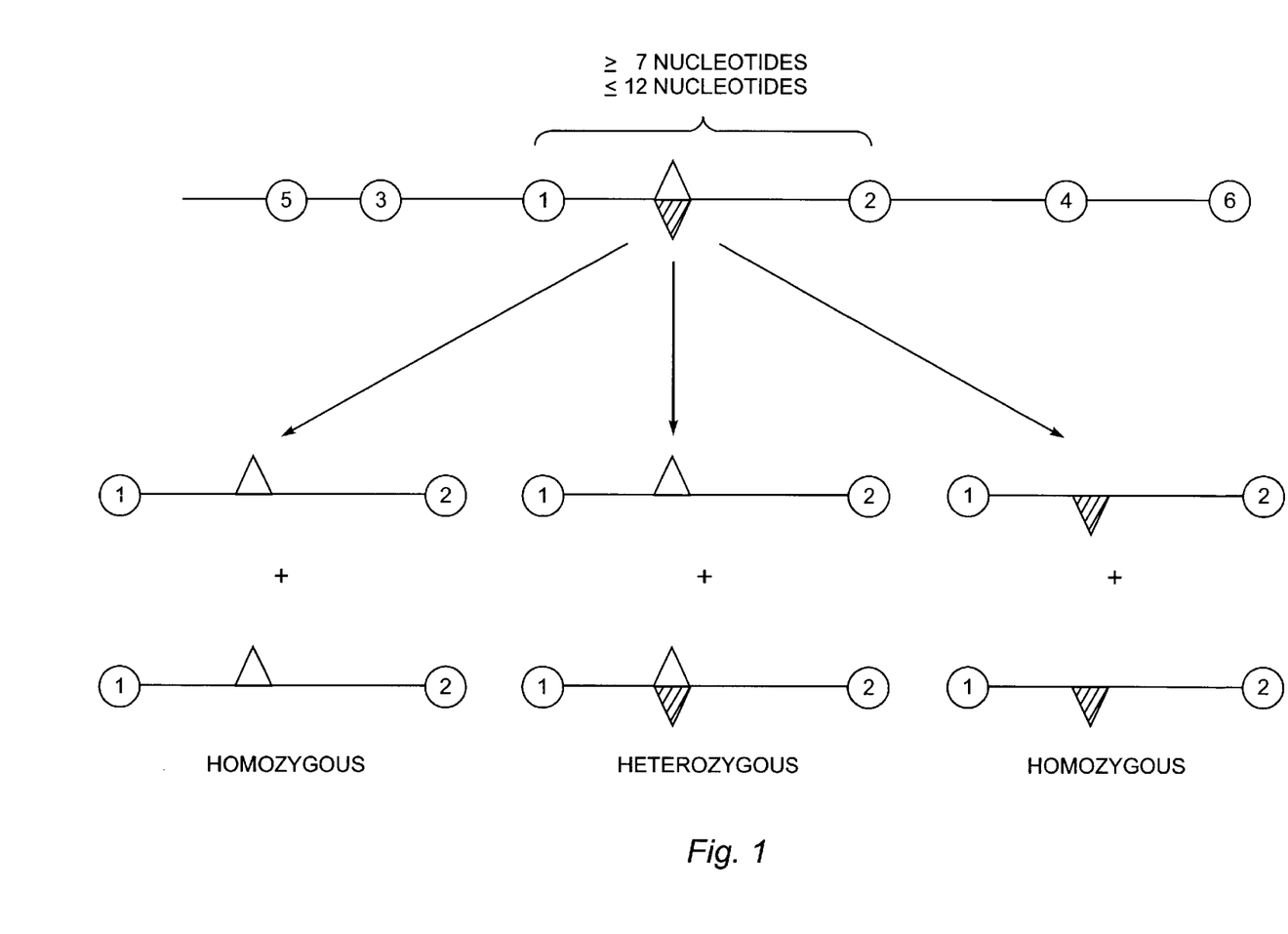
FIG. 1 illustrates the method of this invention when, after replacement of a nucleotide not involved in the target SNP with a modified nucleotide followed by cleavage, a fragment of the presently preferred length is obtained.

In FIG. 1, the bicolor diamond represents the SNP, the white upper portion representing one nucleotide involved in the SNP and the hashed lower portion the other. Thus the upper segment represents both potential alleles. The numbered circles represent the locations of one of the nucleotides not involved in the SNP. As indicated, there are 11 nucleotides, including the SNP, between nucleotides 1 and 2. When these are replaced with modified nucleotides and the modified segments cleaved, two fragments of the same length that may differ only in the mass of the nucleotide at the SNP, will be produced. If, on comparison, the masses of these two fragments are the same, the alleles of the gene in the particular individual from whom they were obtained are homozygous. If the masses are different, the alleles are heterozygous.

If it should occur that neither of the nucleotides that are not involved in the SNP would result in a fragment of from 5 to 20 nucleotides in length, such a fragment may be created as follows.

If the length of the resulting SNP-containing fragment would be greater than 20, then a primer can be used to introduce a nucleotide that will shorten the length of the fragment. That is, a primer can be synthesized that hybridizes with the allelic segment such that a modified base is inserted upstream of the SNP in the primer extension product and is within 20, preferably within 12, nucleotides of the downstream modified base. This can be accomplished by using a primer that contains a point mutation, i.e., a nucleotide mismatch, that corresponds to the downstream modified nucleotide. Cleavage would then occur at the primer-introduced modified nucleotide and at the downstream modified nucleotide to give the desired fragment for comparison. This is illustrated in FIG. 2.

Figure 2:
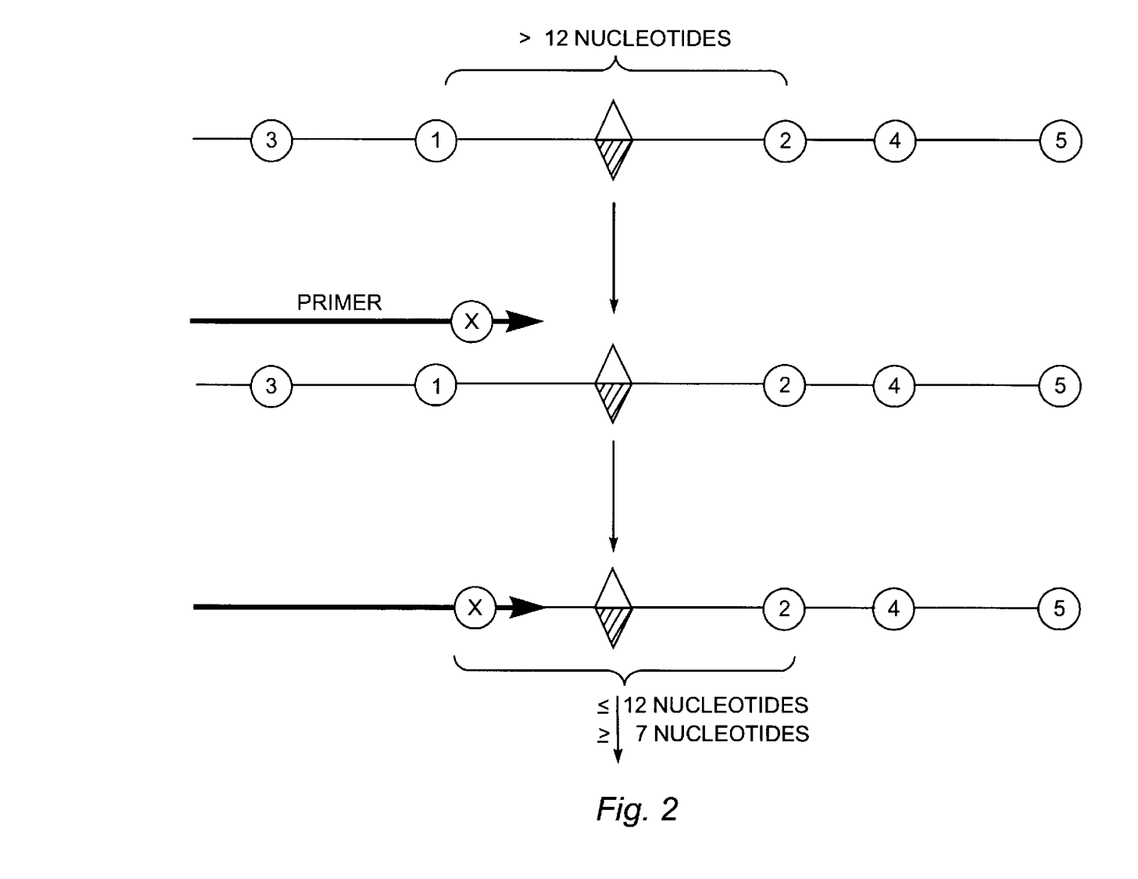
FIG. 2 illustrates the method of this invention wherein neither non-SNP nucleotide will result in a fragment that is 12 or fewer nucleotides in length and a primer is used to artificially create such a fragment.

In FIG. 2, the bicolor diamond represents the SNP, as above. The numbered circles represent the locations of a nucleotide other than one involved in the SNP. As indicated, the number of nucleotides between nucleotide 1 and nucleotide 2 is greater than 12 nucleotides, the presently preferred maximum. (For the purpose of this example, it is assumed that the other non-SNP nucleotide would also result in a fragment longer than 12 or shorter than 7, nucleotides.) A primer is thus synthesized that will hybridize (indicated by the black arrow, the head of which points in the direction of primer extension) such that the nucleotide indicated by the black "X" in the primer will become part of the primer extension product and will occur within 12 nucleotides of downstream modified nucleotide 2. "X" is the same modified nucleotide as 2; thus, the requisite distance between modified nucleotides is created in the primer extension product and the analysis can proceed as above.

If, on the other hand, the SNP-containing fragment would be less than 7, or worse, less than 5, nucleotides in length if either nucleotide that is not involved in the SNP were replaced with a modified nucleotide, a primer can be synthesized that eliminates a site of incorporation of a modified nucleotide. This is illustrated in FIG. 3.

Figure 3:
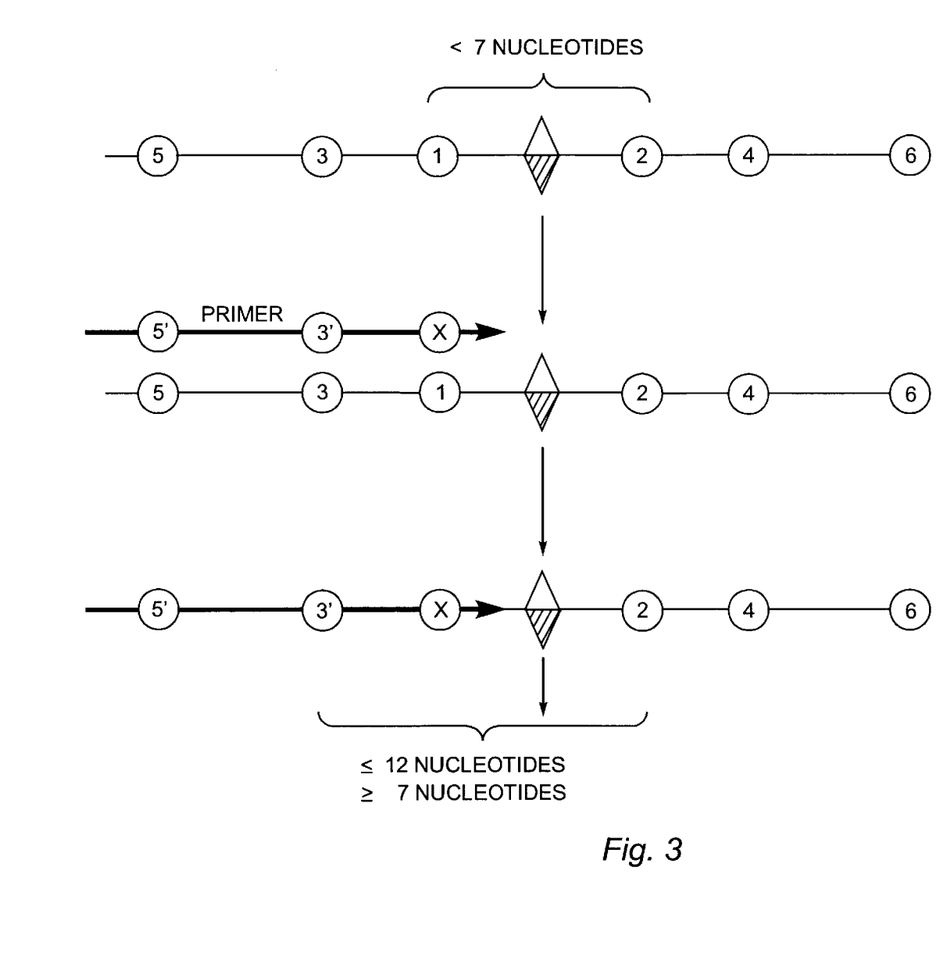
FIG. 3 illustrates the method of this invention wherein neither non-SNP nucleotide will result in a fragment that is 7 nucleotides or more in length and a primer is used to artificially create such a fragment.

In FIG. 3, the bicolor diamond again represents the SNP, the numbered circles represent one of the nucleotides that is not involved in the SNP. (Again, for the sake of this illustration, it is assumed that the other non-SNP nucleotide would likewise lead to a fragment that was greater than or equal to 12 nucleotides long or equal to or shorter than 7 nucleotides.) As can be seen, replacement of the uninvolved nucleotide with a modified nucleotide followed by cleavage would result in a fragment that is too small. Thus, the primer synthesized to extend the segment would be designed to include a base mismatch, indicated by an "X" in the primer sequence, that would replace one of the uninvolved nucleotides with the other uninvolved nucleotide. For example if the SNP is an A/T polymorphism and nucleotides 1 and 2 are C's, then X would be a G and 4 would be a modified C corresponding to nucleotide 3 in the segment. The primer extension product would therefore contain modified nucleotides 2 and 4, which are 7 or more and 12 or less nucleotides apart. Cleavage would then give fragments in the presently preferred range of this invention.

In the above methods, it may be desirable to increase the potential mass difference between the same-length fragments. This is readily accomplished by replacing one of the SNP nucleotides with a mass-modified nucleotide, which does not create a cleavage site but only alters the molecular weight of that nucleotide and therefore the fragment.

In a further embodiment of this invention, the natural nucleotide that is replaced is one of the nucleotides involved in the SNP. Otherwise the method is carried out as indicated above except that the analysis of the fragments involves simply looking for the presence of the 5–20, preferably 7–12, nucleotide fragment. That is, no mass comparison is required. This is illustrated in FIG. 4.

Figure 4:
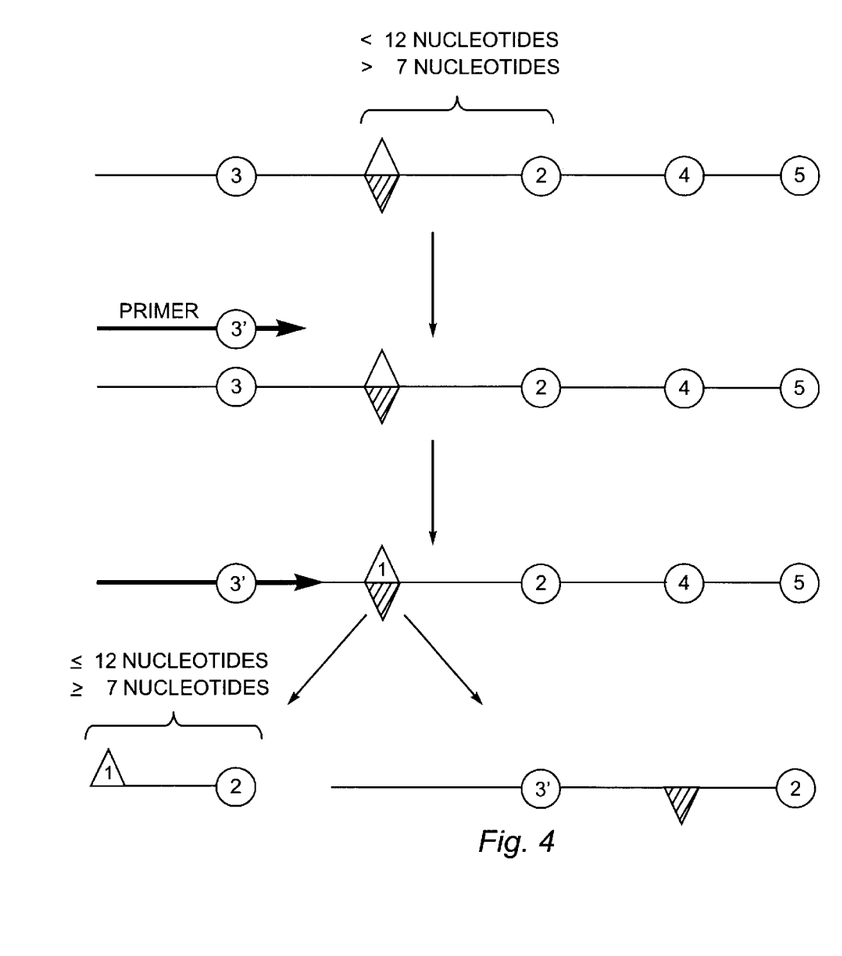
FIG. 4 illustrates the method of this invention wherein one of the SNP nucleotides is 7 or more and 12 or less nucleotides from the next occurrence of the same nucleotide, so that SNP nucleotide is replaced with a modified nucleotide. After cleavage, rather than obtaining two fragments of equal length but different mass, if the SNP nucleotide is present in one of the alleles, a fragment of the desired length will be obtained while, if it is not, the fragment in the vicinity of the SNP will be substantially longer in that it will include the primer.

In FIG. 4, the bicolor diamond again represents the SNP. The numbered circles, however, represent the remaining loci of one of the nucleotides involved in the SNP, for the sake of this example, the SNP nucleotide represented by the upper white portion of the diamond. As can be seen, the white SNP nucleotide is already 7–12 nucleotides from the next same nucleotide. If the white SNP nucleotide is replaced with its counterpart modified nucleotide and cleavage performed, a fragment of a presently preferred length will be obtained. On the other hand, if the other allele has the different hashed nucleotide at the SNP locus, the SNP locus will not be a cleavage site after replacement of the white SNP nucleotide with a modified nucleotide. Thus, after cleavage the hashed nucleotide allele will give a much longer fragment that includes the primer. Thus, all that must be done to genotype the alleles is to look for the shorter fragment. That is, if the shorter fragment is present in one of the sets of fragments but not the other, the alleles are heterozygous. If the shorter nucleotide fragment is observed in both sets of fragments, the alleles are homozygous in the white nucleotide. If the shorter nucleotide fragment is not observed in either set of fragments, the alleles must be homozygous in the black nucleotide.

Although certain embodiments and examples have been used to describe the present invention, it will be apparent to those skilled in the art that changes in the embodiments and examples shown may be made without departing from the scope of this invention.

Other embodiments are contained within the following claims.

What is claimed:

1. A method for genotyping a diploid organism, comprising:
    providing two alleles of a target gene of a diploid organism suspected to contain a polymorphism;
    obtaining a first segment of one allele wherein the segment contains the suspected polymorphic locus;
    obtaining a second segment from the other allele wherein the segment also contains the suspected polymorphic locus;
    replacing a natural nucleotide at greater than 90% of its points of occurrence in the first and the second segment with a modified nucleotide to give a first and a second modified segment; wherein,
       the natural nucleotide that is replaced is not a nucleotide involved in the polymorphism;
       replacing the natural nucleotide with a modified nucleotide comprises amplification using a primer that hybridizes to each segment such that, after amplification, a first modified nucleotide is incorporated between the 3' end of the primer and the polymorphic locus; and, a second modified nucleotide is located from 5 to 20 nucleotides downstream of the first modified nucleotide;

cleaving the first and second modified segments at greater than 90% of the points of occurrence of the modified nucleotide to give a first and second set of fragments each of which comprises a 5–20 nucleotide fragment; and, comparing masses of the 5–20 nucleotide fragments obtained from the first and the second modified segment to detect the presence or absence of the polymorphism.

2. The method of claim 1, wherein the second modified nucleotide is from 7 to 20 nucleotides downstream of the first modified nucleotide; and, the masses of the 7–20 nucleotide fragments obtained from the first and the second modified segment are compared to detect the presence or absence of the polymorphism.

3. The method of claim 1, wherein the second modified nucleotide is from 7 to 12 nucleotides downstream of the first modified nucleotide; and, the masses of the 7–12 nucleotide fragments obtained from the first and the second modified segment are compared to detect the presence or absence of the polymorphism.

4. The method of claim 1, wherein, if there would be less than 5 nucleotides between the first and second modified nucleotides, the method further comprises using a primer that contains a point mutation that removes the site of incorporation of either one of the modified nucleotides.

5. The method of claim 1, wherein, if there are would be less than 7 nucleotides between the first and the second modified nucleotides, the method further comprises using a primer that contains a point mutation that removes the site of incorporation of either one of the modified nucleotides.

6. The method of claim 1, wherein, if there would be more than 20 nucleotides between the first and second modified nucleotides, the method further comprises a primer, which contains a point mutation that incorporates a modified nucleotide downstream of the first modified nucleotide or upstream of the second modified nucleotide.

7. The method of claim 1, wherein, if there would be more than 12 nucleotides between the first and the second modified nucleotides, the method further comprises a primer, which contains a point mutation that incorporates a modified nucleotide downstream of the first modified nucleotide or upstream of the second modified nucleotide.

8. The method of claim 1, further comprising replacing a nucleotide known to occur at the polymorphic site with a mass-modified nucleotide.

9. The method of claim 1, wherein comparing the masses of the fragments comprises using a mass spectrometer.

10. The method of claim 9, wherein the mass spectrometer is a MALDI mass spectrometer.

11. The method of claim 10, wherein the MALDI mass spectrometer is a MALDI-TOF mass spectrometer.

12. The method of claim 9, wherein the mass spectrometer is an ESI mass spectrometer.

13. A method for genotyping a diploid organism, comprising:

providing two alleles of a target gene of a diploid organism suspected to contain a polymorphism;

obtaining a first segment of one allele wherein the segment contains the suspected polymorphic locus;

obtaining a second segment from the other allele wherein the segment also contains the suspected polymorphic locus;

replacing a natural nucleotide at greater than 90% of its points of occurrence in the first and the second segment with a modified nucleotide to give a first and a second modified segment; wherein, the natural nucleotide that is replaced is a nucleotide involved in the polymorphism;

replacing the natural nucleotide with a modified nucleotide comprises amplification using a primer that hybridizes to each segment such that, after amplification, the suspected polymorphic locus is the first site of incorporation of a modified nucleotide after the end of the primer; and, a second modified nucleotide is located from 5 to 20 nucleotides downstream of the first modified nucleotide;

cleaving the first and second modified segments at greater than 90% of the points of occurrence of the modified nucleotide to give a first and second set of fragments; and, comparing masses of the two sets of fragments for the presence of the 5–20 nucleotide fragment wherein, if the fragment is present or absent in both sets, the gene is homozygous and if the fragment is present in only one set, the gene is heterozygous.

14. The method of claim 13, wherein the second modified nucleotide is from 7 to 20 nucleotides downstream of the first modified nucleotide; and, the masses of the two sets of fragments obtained from the first and the second modified segment are compared to detect the presence of the 7–20 nucleotide fragment.

15. The method of claim 13, wherein the second modified nucleotide is from 7 to 12 nucleotides downstream of the first modified nucleotide; and, the masses of the two sets of fragments obtained from the first and the second modified segment are compared to detect the presence of the 7–12 nucleotide fragment.

16. The method of either claim 1 or claim 13, wherein comparing the masses of the fragments comprises using a mass spectrometer.

17. The method of claim 16, wherein the mass spectrometer is a MALDI mass spectrometer.

18. The method of claim 17, wherein the MALDI mass spectrometer is a MALDI-TOF mass spectrometer.

19. The method of claim 16, wherein the mass spectrometer is an ESI mass spectrometer.

20. The method of either claim 1 or claim 13, wherein the percentage replacement of a natural nucleotide with a modified nucleotide, the percentage cleavage at a modified nucleotide, or both the percentage replacement and the percentage cleavage, is greater than 95%.

21. The method of either claim 1 or claim 13, wherein the percentage replacement of a natural nucleotide with a modified nucleotide, the percentage cleavage at a modified nucleotide, or both the percentage replacement and the percentage cleavage, is greater than 99%.

* * * * *